United States Patent [19]

Span

[11] Patent Number: 4,924,781
[45] Date of Patent: * May 15, 1990

[54] PATIENT SUPPORT SYSTEM FOR RADIOTHERAPY

[75] Inventor: Francis J. Span, Eindhoven, Netherlands

[73] Assignee: U.S. Philips Corporation, New York, N.Y.

[*] Notice: The portion of the term of this patent subsequent to Dec. 12, 2006 has been disclaimed.

[21] Appl. No.: 168,353

[22] Filed: Mar. 15, 1988

[30] Foreign Application Priority Data

Mar. 16, 1987 [GB] United Kingdom ............... 8706153

[51] Int. Cl.$^5$ ............................................. A47B 85/00
[52] U.S. Cl. ................................... 108/22; 378/209; 248/122
[58] Field of Search ................... 108/22, 43, 95, 96, 108/139, 140, 141, 144, 148; 5/60; 248/283, 122; 269/322, 325; 378/208, 209, 210, 195, 198

[56] References Cited

U.S. PATENT DOCUMENTS

| | | |
|---|---|---|
| 2,906,143 | 9/1959 | Musser . |
| 3,306,134 | 2/1967 | Winiarski . |
| 3,627,250 | 12/1971 | Pegrum ............................ 378/209 X |
| 4,131,802 | 12/1978 | Braden et al. ................... 269/322 X |
| 4,481,657 | 11/1984 | Larsson ............................... 378/209 |
| 4,609,940 | 9/1986 | Born et al. ...................... 378/209 X |

Primary Examiner—Jose V. Chen
Attorney, Agent, or Firm—William Squire; Thomas A. Briody; Jack E. Haken

[57] ABSTRACT

A patient support system for irradiation therapy or treatment simulation comprises a main arm 1 on a sub-floor mounted pivot 10 about a first vertical axis 17, which supports a further arm 49 rotatable about a second vertical axis 16. At the other end of the arm 49 a vertical pillar 4, pivotable about a third vertical axis 15, supports a vertically displaceable carriage 3 on which a patient support table top 2 is directly mounted. A control system is described which enables x, y coordinate command values to control respective drives associated with the three vertical axes to position a patient quickly and accurately relative to the treatment isocentre. This takes the form of a cartesian error nulling arrangement in which the actual coordinates Xa(act), Ya(act) are computed (143) from angular measurements phi1, phi2 (116A, 104A) about axes 17 and 16, cartesian error signals EX, EY are formed by subtraction (146,147), and angular error signals Ephi1, Ephi2 are derived therefrom to actuate the respective motor drives (131, 132), phi3 being derived from phi1 and phi2 to maintain a steady direction for the table top 2. The system requires only a shallow well while providing a large range of vertical life. Furthermore, no sub-table x-y carriage is required increasing patient accessability.

16 Claims, 5 Drawing Sheets

Fig. 6

$\alpha \equiv \text{ALPHA} \; ; \; \beta \equiv \text{BETA} \; ; \; \emptyset \equiv \text{PHI}.$ $$Xa = X1 + r1 \cdot \cos\emptyset1 + r2 \cdot \cos(\emptyset1 + \emptyset2) + r3 \cdot \cos(\emptyset1 + \emptyset2 + \emptyset3 + \beta) \quad (1)$$

$$Ya = Y1 + r1 \cdot \sin\emptyset1 + r2 \cdot \sin(\emptyset1 + \emptyset2) + r3 \cdot \sin(\emptyset1 + \emptyset2 + \emptyset3 + \beta) \quad (2)$$

$$\alpha = \emptyset1 + \emptyset2 + \emptyset3 \quad (3)$$

$$X(3)a = Xa - X3 = r3 \cdot \cos(\alpha + \beta) \quad (4)$$

$$Y(3)a = Ya - Y3 = r3 \cdot \sin(\alpha + \beta) \quad (5)$$

$$X(1)3 = X3 - X1 = r1 \cdot \cos\emptyset1 + r2 \cdot \cos(\emptyset1 + \emptyset2) \quad (6)$$

$$Y(1)3 = Y3 - Y1 = r1 \cdot \sin\emptyset1 + r2 \cdot \sin(\emptyset1 + \emptyset2) \quad (7)$$

$$Xa = X1 + X(1)3 + X(3)a \quad (8)$$

$$Ya = Y1 + Y(1)3 + Y(3)a \quad (9)$$

$$\frac{\partial X}{\partial \emptyset 1} = -r1\left[\sin\emptyset1 + a \cdot \sin(\emptyset1 + \emptyset2)\right] \quad (10)$$

$$\frac{\partial Y}{\partial \emptyset 1} = r1\left[\cos\emptyset1 + a \cdot \cos(\emptyset1 + \emptyset2)\right] \quad (11)$$

$$a = \frac{r2}{r1} \quad (12)$$

$$\frac{\partial X}{\partial \emptyset 2} = -r2 \cdot \sin(\emptyset1 + \emptyset2) \quad (13)$$

$$\frac{\partial Y}{\partial \emptyset 2} = r2 \cdot \cos(\emptyset1 + \emptyset2) \quad (14)$$

$$E\emptyset1 = EX \cdot \frac{\partial X}{\partial \emptyset 1} + EY \cdot \frac{\partial Y}{\partial \emptyset 1} \quad (15)$$

$$E\emptyset2 = EX \cdot \frac{\partial X}{\partial \emptyset 2} + EY \cdot \frac{\partial Y}{\partial \emptyset 2} \quad (16)$$

$$E\emptyset3 = \alpha - (\emptyset1 + \emptyset2 + \emptyset3) \quad (17)$$

PATIENT SUPPORT SYSTEM FOR RADIOTHERAPY

BACKGROUND OF THE INVENTION

The invention relates to a patient support system for irradiation therapy or treatment simulation, comprising a main supporting arm rotationally attached at one end to a structural support by a first support bearing so as to be rotatable about a first vertical axis fixedly located relative to the treatment isocentre, a patient support table top, interconnecting support means connecting the table top to the other end of the main supporting arm so that the table top can be displaced vertically and horizontally relative to the treatment isocentre and control means for controlling the displacement of the table top.

Radiation therapy involves directing a beam of high energy radiation such as hard x-rays or gamma rays from a suitable source, for example an isotope or a high energy x-ray tube using an electron accelerator, suitably a linear accelerator, at a selected region of the body of a patient in which malignant cells are present. A dosage is employed which is lethal to such cells, however, in order to minimise damage to other parts of the body, the dose applied to the surrounding tissue is reduced by rotating the direction of the irradiation beam about a central point called the treatment isocentre, which is located at or near the centre of the selected body region to be irradiated.

For this purpose a source of high energy radiation is mounted in counterbalanced manner on a gantry so as to be capable of rotation about a horizontal axis through the isocentre. The source is heavily screened to reduce generally emitted radiation to a reasonably safe amount and the emergent irradiation beam is limited by a diaphragm which defines the boundaries of the region of the patient to be irradiated, in a manner such that radiation is generally directed radially towards the isocentre. The source and gantry assembly is consequently very massive and is normally fixed to the structure of the associated building. This means that the isocentre is fixed in space within the treatment room. It is therefore a requirement for a patient support system that it should be capable of supporting and displacing a patient in an accurate and reproducible manner so that any body region to be irradiated can be located at the isocentre and positioned relative to the scanning arc of the radiation source so that irradiation may be applied to the patient along selectable directions of incidence.

A presently used form of patient support system of the kind referred to comprises a floor mounted relatively small turntable which is rotatable about a vertical axis usually through the isocentre and supports a radial arm extension the outer end of which is connected to a patient support table top by interconnecting support means in the form of a rotatably mounted pedestal base having an under table lift for vertical displacement and on the top of which is mounted a carriage assembly formed by a tandem arrangement of respective lateral and longitudinal horizontal displacement carriages, the table top being attached to the uppermost carriage. This form of patient support typically employs a form of scissors jack to provide the lift. Because of the relatively short stroke obtainable by such a jack and the need for a low minimum table height of about 70 cm for the convenience of patient access to the table top, this results in a relatively low maximum lifting height of about 120 cms. The maximum lifting height can be raised by the use of an underfloor pit. In some high energy installations the isocentre is even higher and a larger range of height adjustment can be provided using a hydraulic ram lift mounted on a more extensive turntable. This, however, requires the presence of a correspondingly deep underfloor pit to accommodate the ram housing resulting in higher installation costs and may not in some cases be structurally possible.

A further disadvantage of the above described patient support system concerns the carriage assembly for providing the horizontal displacement of the table top in two dimensions since the carriages and associated parallel rails render the assembly bulky and heavy, and tend to restrict access to the patient.

Our copending U.S. patent application Ser. No. 168,354, now U.S. Pat. No. 4,885,998 filed concurrently with this application, seeks to provide an improved patient support system for irradiation therapy which can reduce these difficulties and can be simple and convenient to operate in conjunction with computer controlled treatment or simulation equipment.

The patient support system disclosed therein comprises a main supporting arm rotationally attached at one end to a structural support by a first support bearing so as to be rotatable about a first vertical axis fixedly located relative to the treatment isocentre, a further supporting arm rotationally attached at one end to the other end of the main supporting arm by a second support bearing so as to be rotatable about a second vertical axis, vertical support means rotationally attached to the other end of the further supporting arm by a third support bearing so as to be rotatable about a third vertical axis, and a patient support table top attached to supporting carrier means, the vertical support means including means for locating and vertically displacing the supporting carrier means.

Control of the positioning of a patient support table top employed for irradiation therapy or treatment simulation, is usually carried out with reference to a set of cartesian coordinate axes in which the Z-axis is taken as being vertical and the origin is normally taken to coincide with the treatment isocentre.

In the course of treatment it is generally necessary to position and reposition a patient so that one or more selected regions of the body can be irradiated and, if necessary, displaced during irradiation, for example to treat an extensive region or to avoid irradiating an adjacent important healthy region while the irradiation beam source is being angularly displaced on the gantry.

In the case of the present table support system, measurements relating to the horizontal positioning of the patient are derived from respective angular displacement sensors coupled to respective shafts associated with relative angular displacements about the first, second and third vertical axes, and subsequent horizontal displacement of the patient support table top is effected by motor drives respectively arranged to modify these angular displacements. This introduces a difficulty in that, although a given arbitary combination of measured angular values can be accurately and rapidly converted by calculation into a corresponding pair of X- and Y-coordinate values relating to a reference point in a patient, it is not simple from a mathematical point of view to convert an arbitrary pair of X- and Y-coordinate demand values into a corresponding set of angular demand values for servo control of the motor drives about the three vertical axes, directly, with sufficient accuracy and speed to enable the patient support table top to be controlled in real time, while the use of a look-up table of sufficient accuracy would employ a prohibitive amount of memory.

SUMMARY OF THE INVENTION

It is an object of the invention to provide a patient support system of the kind referred to in which the angular drive motors can be readily controlled in response to cartesian coordinate demand values.

According to the invention there is provided a patient support system for irradiation therapy or treatment simulation, comprising a main supporting arm rotationally attached at one end to a structural support by a first support bearing so as to be rotatable about a first vertical axis fixedly located relative to the treatment isocentre, a further supporting arm rotationally attached at one end to the other end of the main supporting arm by a second support bearing so as to be rotatable about a second vertical axis, vertical support means rotationally attached to the other end of the further supporting arm by a third support bearing so as to be rotatable about a third vertical axis, the first, second and third support bearings each being provided with corresponding motor drives and associated output shaft angular position and velocity sensing means, a patient support table top attached to supporting carrier means, the vertical support means including means for locating and vertically displacing the supporting carrier means, and control means including computing means arranged to control the respective motor drives in response to the output of the associated sensing means and to corresponding position demand values, characterised in that the position demand values include horizontal X- and Y-coordinate set-point demand-values for a predetermined reference point associated with a patient on the patient support table top, relative to the treatment isocentre, said computing means being arranged to calculate actual X- and Y-coordinate values relating to said reference point from angular positions measured by angular position sensors respectively associated with relative angular displacement about at least the first and second vertical axes, to compare these actual coordinate values using a differencing process, with the corresponding set-point cartesian coordinate demand values to form corresponding cartesian error values and to combine the corresponding cartesian error values with the appropriate polarity in each case, so as to provide corresponding drive signals for the motor drives associated with rotation about said vertical axes so as to form a cartesian error nulling arrangement which reduces or nullifies said cartesian error values.

The motor drives can include electric drive motors to provide motive power and would also include reduction gearing. In servo drives it is also usual to include a velocity sensor on the motor shaft to provide a velocity feedback signal unaffected by mechanical backlash. The computing means can comprise a small digital computer, or one or more microprocessor systems or it can comprise dedicated computing hardware connected together to provide the hereinafter described operations.

The control means can include a look-up table provided in a matrix organised memory which is addressed in accordance with cartesian coordinate demand values and which stores coarse set-point values for the angular positions about at least the first and second vertical axes for spaced spot values of pairs of X- and Y-coordinates over an operational field of values, so that when either of the cartesian error values exceeds a predetermined threshold the respective coarse set-point angular position values recalled from memory can be employed as demand values for the motor drives arranged as corresponding angular position set-point servos. The appropriate polarity of a respective cartesian error component of each of the corresponding drive signals for the cartesian error nulling arrangement, can be selected by multiplying that cartesian error value by the partial differential coefficient relating to that cartesian coordinate with respect to the angular displacement to which the drive relates, before combining it with the similarly processed other cartesian error component and these differential coefficients can be derived from the actual measured values of the respective angular positions. Alternatively, a look-up table can be provided in a matrix organised memory which is addressed in accordance with cartesian coordinate demand values and which stores data representing the appropriate polarity for respective cartesian coordinate error components of each of the corresponding drive signals for the motor drives associated with rotation about said vertical axes in the cartesian error nulling arrangement, for spaced spot values of pairs of X- and Y-coordinates over an operational field of values. It is usual to preselect the horizontal angle alpha between the longitudinal axis of the patient support table top and the direction of the X-coordinate axis which latter coincides with the rotation axis of the supporting gantry of an associated high energy radiation generator, and this angle can be stored by the control means. The motor drive associated with angular displacement of the vertical support means about the third vertical axis relative to the further supporting arm, can then be arranged as an angular position set-point servo so as to maintain the measured angular position phi3 about this third vertical axis, of the longitudinal axis of the patient support table top relative to the further supporting arm, equal to alpha plus 360 degrees reduced by the measured relative angle phi2 about the second vertical axis between the main supporting arm and the further supporting arm, and by the measured relative angle phi1 about the first vertical axis between the main supporting arm and the X-coordinate direction in order to maintain the axial direction of the table top steady in space.

BRIEF DESCRIPTION OF THE DRAWING

Embodiments of the invention will now be described by way of example, with reference to the accompanying drawings of which:

FIG. 5 is a block diagram illustrating a control arrangement for the patient support system in accordance with the invention and FIG. 6 is a series of equations applicable to transformations in the control arrangement of FIG. 5.

DETAILED DESCRIPTION OF THE PREFERRED EMBODIMENT

Figure 1:
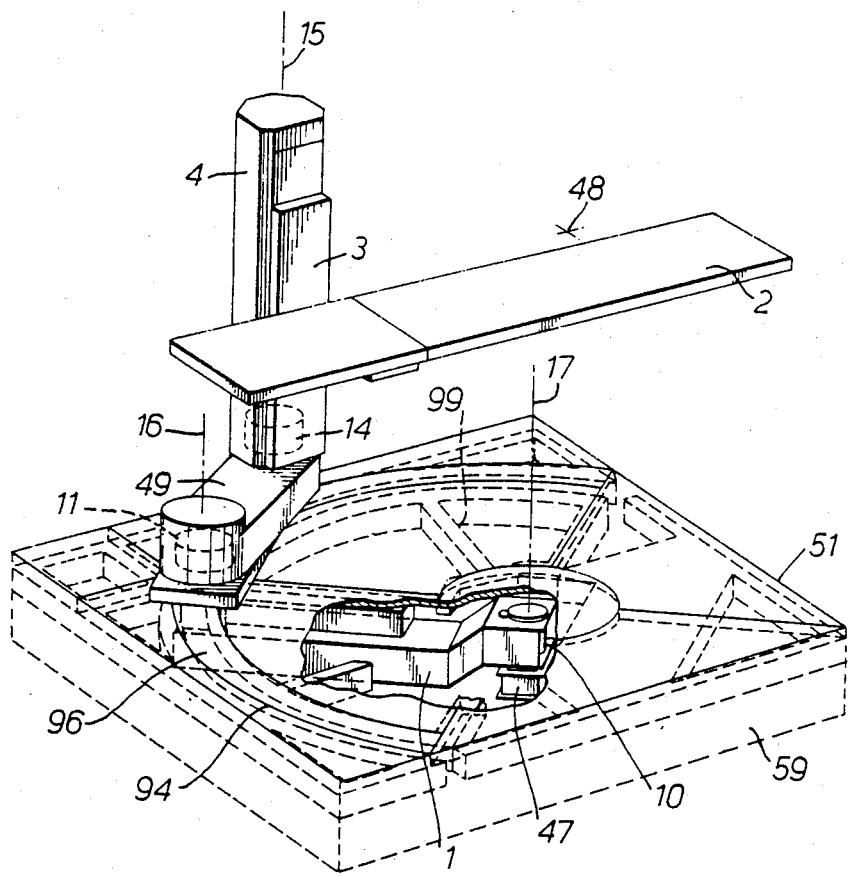
FIG. 1 is a perspective view, partly cut away, illustrating diagrammatically a patient support system in accordance with the invention.

Reference will now be made to FIG. 1 which illustrates a patient support system for irradiation therapy or treatment simulation in accordance with the invention described and claimed in our copending U.K. Patent Application. A main supporting arm 1 is rotationally attached at one end by means of a first support bearing 10, suitably two spaced heavy duty single race ball bearings, to a structural support in the form of an underfloor mounting frame 47 fixed to the substructure of the floor 51 of the treatment room in a shallow well 59, so as to be rotatable about a first vertical axis 17. The axis 17 can, if desired, pass through the treatment isocentre 48 of an associated counterbalanced gantry-mounted high-energy irradiation source (not shown), but will in any event be fixed relative thereto since the irradiation source gantry will also be fixedly attached to the structure of the treatment building. A patient support 2 is connected to the other end of the main supporting arm 1 by interconnecting support means 4, 49, so that the table top 2 can be displaced vertically and horizontally relative to the treatment isocentre 48.

The interconnecting support means comprise a further supporting arm 49 rotationally attached at one end to the unsupported end of the main supporting arm 1 by means of a second support bearing 11, suitably in the form of two spaced single race ball bearings, so as to be rotatable about a second vertical axis 16, and vertical support means in the form of a single vertical supporting pillar 4 rotationally attached to the other end of the further supporting arm 49 by a third support bearing 14, suitably in the form of two spaced single race ball bearings, so as to be rotatable about a third vertical axis 15. The patient support table top 2 is attached to supporting carrier means in the form of a vertically displaceable carriage 3, and the pillar 4 includes means for locating and vertically displacing the carriage 3.

Figure 2:
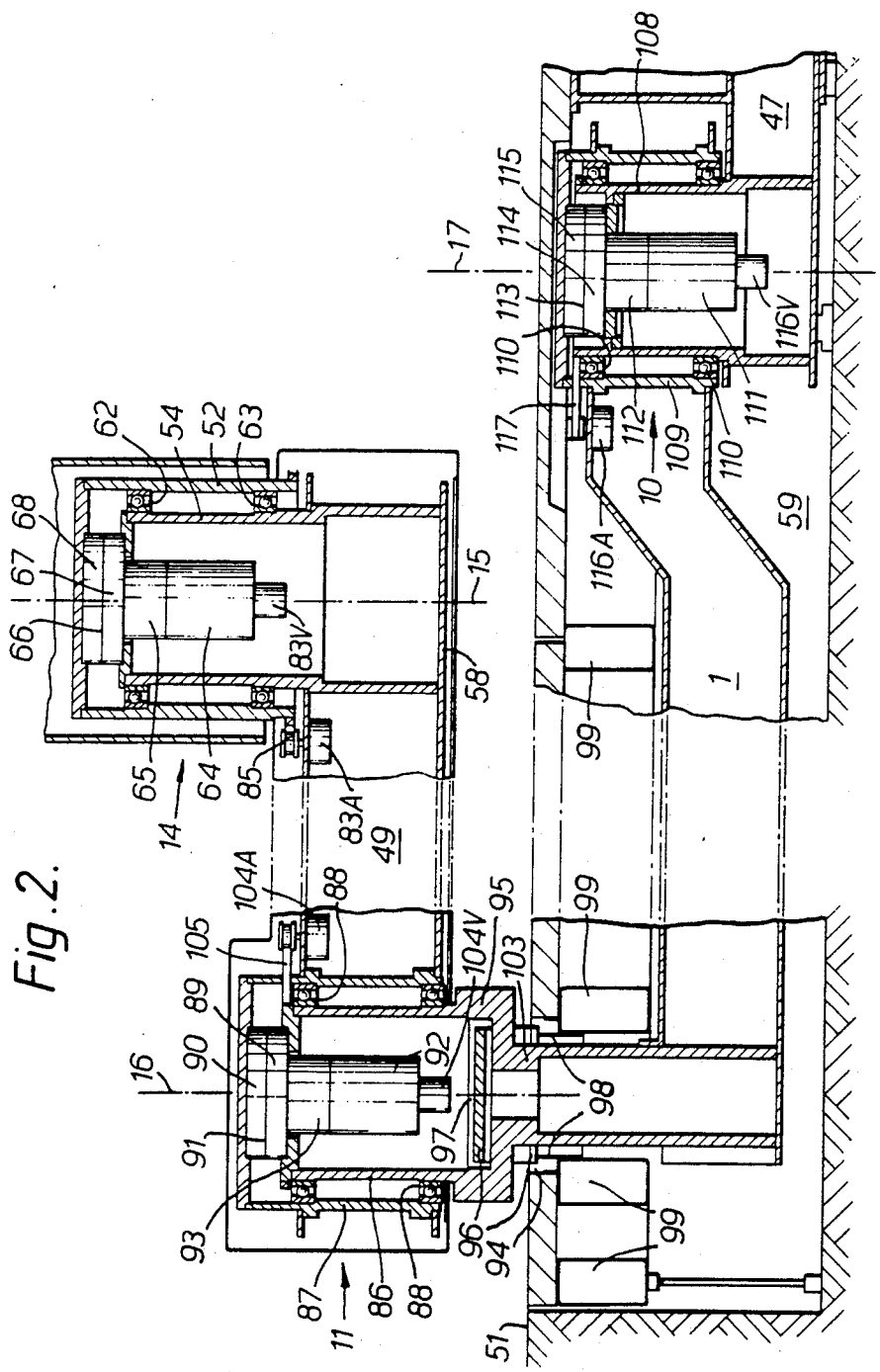
FIG. 2 is a diagrammatic vertical section illustrating part of the supporting arm assembly of FIG. 1.

Referring to FIG. 2, the lower end of the pillar 4 is rigidly attached to the outer cylindrical member 52 of the third support bearing 14, suitably by hole welding. The cylindrical member 52 thus forms the transverse stiffening member for the lower end of the pillar 4. The inner cylindrical member 54 of the third support bearing 14, is rigidly fixed, suitably by hole welding, to the load bearing beam 58 of the further support arm 49. The cylindrical bearing members 52 and 54 are coaxial and are rotatably connected via two spaced ball-races 62, 63.

Rotation of the pillar 4 relative to the further supporting arm 49, about the third vertical axis 15, is effected by means of a motor drive suitably comprising an electric motor 64 with reduction gear box 65 driving a harmonic drive 66 connected between the inner and outer cylindrical bearing members 52 and 54. One form of harmonic drive is described in U.S. Pat. No. 2,906,143.

The harmonic drive 66 shown in FIG. 2, preferably employs a form of strain wave gearing arrangement described in said U.S. Pat. No. 2,906,143. The drive housing is constructed in two parts 67, 68, which are rotatable relative to one another about a vertical axis, namely the third vertical axis 15. One part 67 is secured to the inner cylindrical member 54 of the third support bearing 14 and to one of the annular members of the harmonic drive so as to form one side of the output drive of the strain wave gear. The other part 68 is secured to the outer cylindrical member 52 of the bearing 14 and to the other annular member of the drive so as to form the other side of the output drive. The output from the motor 64 and the gearbox 65 drives the input shaft and hence the strain inducing element of the harmonic drive. The housing of the motor 64 and the gearbox 65 is connected to the part 67 for convenience, but could equally well be connected to the other part 68 if desired.

The relative angular displacement of the pillar 4 about the third vertical axis 15 relative to the further supporting arm 49 is sensed by an angular position sensor 83A which is mounted on the further supporting arm 49 and is driven via a toothed belt 85 the ends of which are attached to a point on a circumferential region at the lower end of the outer cylindrical member 52 of the third support bearing 14. An angular velocity sensor 83V is conveniently included on the shaft of the drive motor 64.

The second support bearing 11 which connects the unsupported end of the main supporting arm 1 to that end of the further supporting arm 49 which is distant from the pillar 4, is basically similar in construction to that of the third support bearing 14. Thus the bearing comprises inner and outer coaxial cylindrical bearing members 86, 87, connected by a spaced pair of ball-races 88 for relative angular displacement about the second vertical axis 16, and rigidly connected to respective output drive parts 89, 90, of a harmonic drive gearbox 91, preferably formed as in the case of the drive 66 by a diametrically induced strain wave gearing arrangement, which together with a motor, suitably an electric drive motor 92 provided with an angular velocity sensor 104V and a reduction gearbox 93 form a motor drive for angularly displacing the arm 49 relative to the main arm 1 about the second vertical axis 16. The load bearing beam 58 of the arm 49 is rigidly attached, suitably by hole welding, to the outer bearing member 87.

The relative angle between the arms 1 and 49 is sensed by a sensor 104A mounted on the beam 58 and driven via a toothed belt 105 from the upper rim of the inner bearing member 86 via a slot in the outer bearing member 87.

The main supporting arm 1 is located below the surface of the floor 51 of the treatment room and an arcuate aperture 94 is provided in the floor surface to accommodate connecting means in the form of a supporting extension 95 to the inner bearing member 86, which is rigidly attached to the main supporting arm 1 suitably by hole welding. The arcuate aperture 94 in the floor 51 is covered by a flexible cover strip 96 which is passed through a passageway 97 through the supporting extension 95.

The flexible strip 96 is generally arcuate in plan view as can be seen from FIG. 1, and in order to provide a secure surface for standing on, the strip 96 comprises a plurality of transversely arranged load-bearing segments, virtually strips, (not shown), flexibly linked to one another, and the inner and outer sides of the arcuate aperture 94 are each provided with a supporting ledge 98 fixedly attached to a floor-supporting frame 99, and arranged so that each segment resting thereon is supported at each end by a corresponding ledge 98 with the upper surface of the flexible cover strip 96 flush with the surface 51 of the floor.

The first support bearing 10 which supports the main arm 1, is of similar construction to that of the second and third support bearings 11, 14, although it must have a slightly heavier loading capacity than the others. The bearing 10 comprises inner and outer coaxial cylindrical bearing members 108, 109, connected by a spaced pair of heavy duty single race ball bearings 110 for the angular displacement of the main arm 1 about the first vertical axis 17. The inner bearing member 108 is rigidly fixed to the underfloor mounting frame 47 which is itself attached to the substructure of the floor 51 in the well 59. The outer bearing member 109 is fixedly attached to the arm 1, suitably by hole welding. Rotary displacement of the arm 1 about the axis 17 is effected by means of a motor drive suitably comprising an electric motor 111 provided with a velocity sensor 116V, a reduction gearbox 112 and a harmonic drive gearbox 113. The harmonic drive preferably comprises a strain wave gearing arrangement using a symmetrical two lobed (elliptical) strain inducer as hereinbefore described and the respective output drive parts 114, 115 thereof are rigidly connected to the inner and outer cylindrical bearing members 108, 109, respectively. The angular displacement of the arm 1 about the first vertical axis 17, is sensed by a sensor 116A mounted on the main arm 1 and driven via a toothed belt 117 attached at both ends to respective points on an upper rim of the inner bearing member 108 via a slot-like aperture in the outer bearing member 109. Because of the stresses involved, the surface of the teeth in the harmonic drive must be suitably hardened without adversely affecting the flexibility of the inner annular output drive component.

It would be usual to provide touch sensitive switching members especially at floor level for operating an electrical cut out for the drive motors should a collision occur with the operator or other obstruction during displacement.

The relative lengths of the main and further supporting arms 1 and 49 are preferably chosen so that the longitudinal stroke which the further supporting arm 49 is required to perform to locate any point along the table top and hence in a patient, at the treatment isocentre for the operational range of values for the angle alpha of say −70 degrees to +70 degrees, can be achieved with a reasonable angular displacement of about 90 degrees about the second vertical axis 16. The length of the main supporting arm 1 in combination with the length of the further arm 49, is preferably arranged so that the pillar 4 can be readily maintained just clear of the region which is swept by the head of the high energy radiation source, usually a linear accelerator, or of the simulation radiographic head and image section, during a normal irradiation treatment or simulation.

Suitable forms of control arrangement will now be considered which enable the treatment region of a patient supported by the support table top 2 to be readily positioned in the treatment zone about the isocentre in response to an operator command or a suitable stored treatment program.

Each of the motor drives which in the present example are assumed to be actuated by electric drive motors, can be arranged as a form of set-point servo in which a set-point input value representing a vertical position Z in the case of a motor drive, now shown, but arranged to displace the carriage 3 vertically, or a relative angular displacement in the case of the drives for the support bearings 10, 11 and 14, is compared in a comparator or by some other process of subtraction, with an actual value measured by an associated sensor, to provide an error signal to drive the corresponding motor in a direction which will reduce the error. The usual servo techniques of velocity feedback for damping oscillations and of integration and feed-forward for reducing steady state errors, can be employed as and where necessary to increase accuracy. A patient support system in accordance with the invention, is provided with coordinated control means which can suitably include a computer or one or more microprocessors, to control the electric motor drives which provide the angular displacements about the first, second and third vertical axes 17, 16 and 15, and the vertical displacement of the carriage 3 in response to the associated position sensing means 116A, 104A, 83A and 33A, and to set-point demand values corresponding to demand position commands which the operator can provide directly as an instruction, for example via a keypad, or which can be generated by computer means for example from a therapy treatment program.

Figure 3:
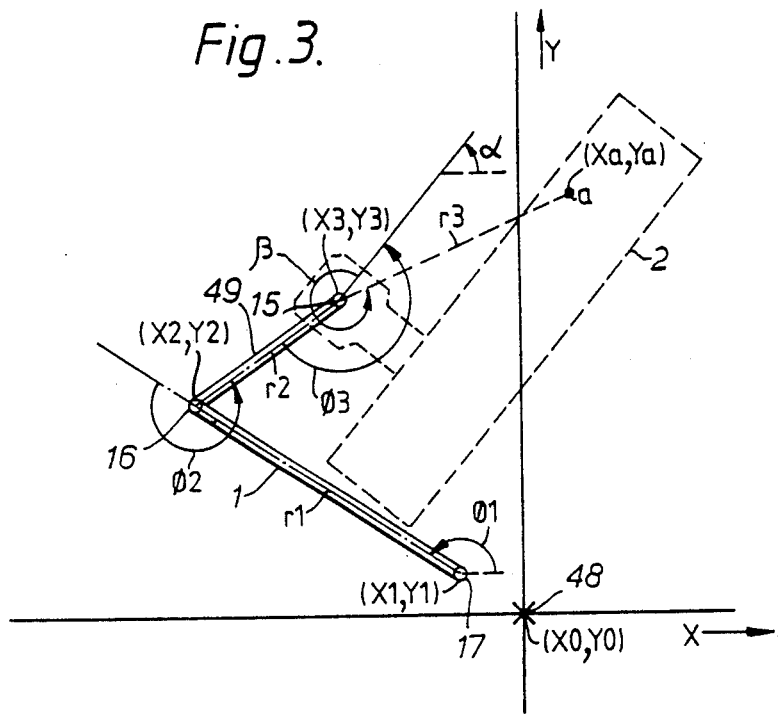
FIG. 3 is a diagram illustrating geometrically the control parameters.

FIG. 3 is a diagram which illustrates the relationship between the components of the patient support system of FIG. 1 and those geometrical parameters relating to a horizontal plane which are employed for the control of the relative motor drives and for defining a dynamic treatment program relative to the isocentre. It is usual in irradiation therapy to define the patient position in a cartesian coordinate system with the origin X0, Y0, Z0, at the isocentre of the high-energy source gantry. It is also usual to define an angle alpha as the angle between the longitudinal axis of the patient support table top 2 and the rotation axis of the gantry which latter is also directed along the X-axis. The Z-axis is the vertical axis. The patient position is taken as a specified point, usually at or near the centre of a region in the patient which is to receive treatment, and is indicated by the reference point a in FIG. 3.

The horizontal coordinates of the first vertical axis 17 are X1, Y1, and can if desired, lie at the origin X0, Y0 although this is not essential since a constant offset of (X1-X0), (Y1-Y0), can be simply applied to any calculations in the X-Y plane. The angular position phi1 of the main supporting arm 1 is measured anticlockwise from the X-axis and the second vertical axis 16 is spaced a distance r1 from the first. The angular position phi2 of the further supporting arm 49 is measured anticlockwise from an in-line position relative to the main arm 1. The third vertical axis 15 is spaced a distance r2 from the second axis 16, and the angular position phi3 of the longitudinal axis of the table top is measured from a direction parallel to the arm 49 in an anticlockwise direction as indicated. The coordinate positions of the second and third vertical axes in the X-Y plane are identified as X2, Y2, and X3, Y3, respectively, and will vary with the horizontal adjustment of the table top relative to the first vertical axis X1, Y1 which is permanently fixed.

The reference point a in the treatment region of a patient located on the table top 2, is a horizontal radial distance r3 from the third vertical axis 15 at the point X3, Y3, and the connecting line r3 is inclined at an angle beta measured in an anticlockwise direction about the third vertical axis 15 from the direction of the longitudinal axis of the table top. It should be noted that while r1 and r2 are fixed quantities determined by the apparatus, the values of r3 and beta will vary in an arbitrary manner from one treatment to another and must be determined by the system each time a patient is placed on the table top 2. This can be carried out by manually controlling the support system until the point a, indicated in practice by a visible mark applied to the upper surface of the patient, coincides with the origin X0, Y0 as indicated optically by a light beam projector (not shown) in the high-energy treatment head which latter is orientated on the gantry (not shown) to project the light beam vertically. In this position of the patient, the X and Y coordinates of the point X3, Y3 representing the third vertical axis 15, are determined from the measured values of the angular positions phi1 and phi2 provided by the angular position sensors 116A and 104A, the known constant values of r1 and r2, and the fixed offset between the origin X0 and Y0 and the coordinates X1, Y1 of the first vertical axis 17. From the geometry of the arrangement and the operational requirement that the table axis must be inclined by a preset angle alpha which can be zero, to the x-axis, the angle phi3 must be maintained, e.g. by set-point servo control, so that the sum of phi1, phi2 and phi3 always equals alpha (+360 degrees). From this data is is a simple process to compute the values of the distance r3 and the angle beta for example using equations 4 and 5 on the accompanying sheet of equations, and to store the values for use during the course of the subsequent treatment of simulation. In a similar manner, the vertical origin Z0 is determined by reorienting the gantry so that the high-energy source head projects the light beam horizontally and the vertical drive motor, not shown, is energised so as to make a further optical mark applied to the side of the patient coincide with the projected reference beam. The value which is then read out from a corresponding vertical position sensor, is stored as the position of the origin Z0 for the subsequent treatment or simulation.

The coordinated control of the patient support system in accordance with the invention is arranged so that the respective electric motor drives employing the motors 111, 92 and 64 which provide corresponding angular displacements about the first, second and third vertical axes 17, 16, 15, are controlled, preferably by computer means, so as to provide X- and Y-coordinate set-point demand-value control of the patient support table top. The problem of providing sets of three set-point angle values phi1, phi2 and phi3 to the required accuracy to control the associated angular displacement servos, from corresponding parts of set-point coordinates Xa(setp), Ya(setp) provided either by manual input from an operator or in a sequence of demand values in cartesian coordinates which represent steps in a program for table top displacement during a treatment or a simulation, can be solved in various ways.

A direct X-Y to angle phi 1, 2, 3 mathematical coordinate transformation could be attempted. Such a transformation would be non-linear and could be very difficult if not impossible to formulate to the desired accuracy in a practically useful manner. Alternatively, an iterative process of numerical approximation could be attempted, but this could take too long to achieve the required accuracy for use as a real time process on a computer or microprocessor. A look-up table could be employed, however, for a positional accuracy of 0.1 mm in 1 m some 400M to 600M bytes of storage would be required. If a much coarser look up table with, for example, ten base points for each horizontal coordinate, were employed and interpolation carried out using stored base point angles and X and Y angular gradients for each angle phi1, phi2 and phi3, as little as 4K bytes of memory could be employed, but the overall accuracy of the interpolation will be very dependent on position and can become unacceptable for certain combinations of angular values.

The reverse coordinate transformation which enables the actual horizontal cartesian coordinates Xa(act), Ya(act) of the patient reference point a to be calculated from present angular values phi1(act), phi2(act) and phi3(act) measured by the data sensors 116A, 104A and 83A, is however much easier to process to the required accuracy in real time by a computer or microprocessor. A generalized form of this reverse transformation is given by equations (1), (2) and (3) in FIG. 6. Present values Xa(act), Ya(act) computed using these equations, can be compared by a process of subtraction with momentary set-point demand values Xa(setp), Ya(setp) provided for example by a treatment program displacement sequence, to generate error (i.e. difference) values EX, EY. These difference values can used when combined in accordance with an appropriate polarity, to provide angular error drive signals for respective open-loop angular drive servos to provide a suitable nulling servo arrangement. However, such an attempt to control two or more operationally independent but globally interrelated angular displacement variables can give rise to control and stability problems when the initial cartesian errors are too large. It is therefore desirable to provide a coarse initial positioning control arrangement based on a look-up table to bring the angular drive servos to within a few degrees of the correct position before enabling the nulling arrangement to operate.

As hereinbefore mentioned in relation to the setting-up procedure and as shown by equation (3), the motor drive 64, 65, 66 which alters phi3 is arranged as an angular-value set-point servo controlled by the difference between the angular value alpha (+360 degrees) and the sum of phi1(act) and phi2(act). By operating on the actual momentary values of phi1 and phi2, the orientation of the longitudinal axis of the patient support table is maintained constant in space for a constant value of alpha so that the patient does not suffer an undesirable yawing motion as the angles phi1 and phi2 are altered, possibly at different rates, by the nulling servo arrangement. As a further beneficial consequence, the nulling servo will only have to operate on the phi1 and phi2 drives.

The transformation defined by equations (1) and (2) may be further simplified by noting that the coordinates X1, Y1 are fixed relative to the origin X0, Y0, and for a given treatment or simulation, the last term containing r3 which represents a further offset of X3, Y3 from Xa, Ya, will only vary if the angle alpha is varied since r3 and beta are measured during the setting up procedure and remain constant during a treatment or simulation run. This is indicated by equations (4) and (5). This means that the first and last terms X1, Y1 and X(3)a, Y(3)a can be regarded as constant offsets (unless alpha varies in the latter case) for the purpose of processing the transformation data. Thus the reverse transformation can be simplified as illustrated by equations (6) and (7) to which these constants can be added as in equations (8) and (9), so that only the drives which control phi1 and phi2 require to be included in the nulling servo arrangement. FIG. 9 illustrates the displacements.

Figure 5:
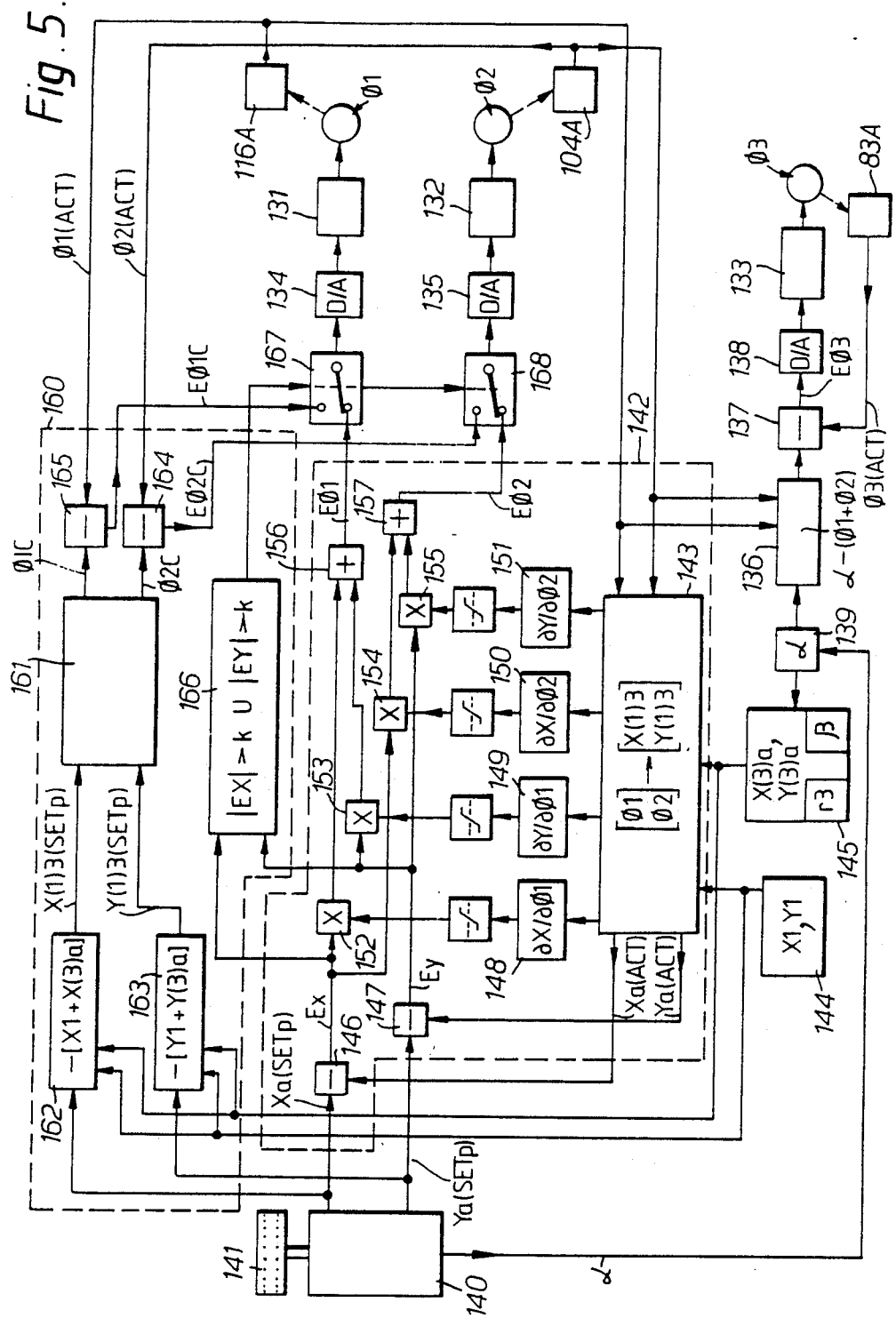

One form of coordinated control arrangement for a three-axis patient support system in accordance with the invention is illustrated diagrammatically in FIG. 5 (which is partly a flow diagram for the processing of data) in which most of the blocks represent arithmetical operations which can be carried out digitally by a computer or microprocessor in a programmed sequence related to a data sampling cycle controlling the aquisition of angular position data and programmed set-point demand values. Alternatively some or all of the blocks can be implemented by corresponding hardware elements.

The angular displacements phi1, phi2 and phi3 are effected by servo systems represented by blocks 131, 132 and 133 respectively. Each servo system includes the corresponding velocity sensor which provides a velocity feedback loop to supply damping. This is preferably performed using analogue signals to provide a smooth control undisturbed by the sampling effects of a digital system. A further velocity signal can be provided as a feed forward signal by the coordinated control system, in order to overcome steady state velocity errors, if desired. The servos 131 and 132 are arranged in a final nulling process of error reduction, as open loop servos, and are controlled by a corresponding input error (drive) signal Ephi1 an Ephi2 via a respective digital-to-analog converter 134, 135. The derivation of these drive signals in the overall nulling system and coarse error-reduction system, will be described later. The servo 133 is a set-point servo which is arranged to make phi3(act) measured by the data sensor 83A, equal to the difference between alpha and the sum of phi1(act) and phi2(act) obtained by a computing process indicated by the block 136. The result from 136 is applied with the output from 83A to a differencing process 137 to detect any error Ephi3 in accordance with equation (17) in which the measured actual values are employed. The actual values and the processes 136 and 137 are preferably carried out digitally to a sufficient degree of accuracy, and the error signal Ephi3 is then converted by a digital-to-analog converter 138 to provide the analog error drive signal for the servo 133. The momentary value representing the angle alpha, block 139, is stored at an available location in memory and may be a value provided by the operator at the start of an operation, or may be the present value from a sequence of values forming part of a treatment or simulation control program. The general control and operating system is indicated by the block 140, and a manual input keyboard 141 is provided. The system 140 can comprise a small general purpose computer or can be made up of one or more microprocessor based systems.

The dashed line boundary 142 indicates the processes involved in the nulling servo arrangement, by means of which set-point coordinate values Xa(setp) and Ya(setp) demanded via the control system 140 by the operator or by a treatment or simulation program, are converted into corresponding angular positions phi1 and phi2 by the open loop servos 131 and 132.

Figure 4:
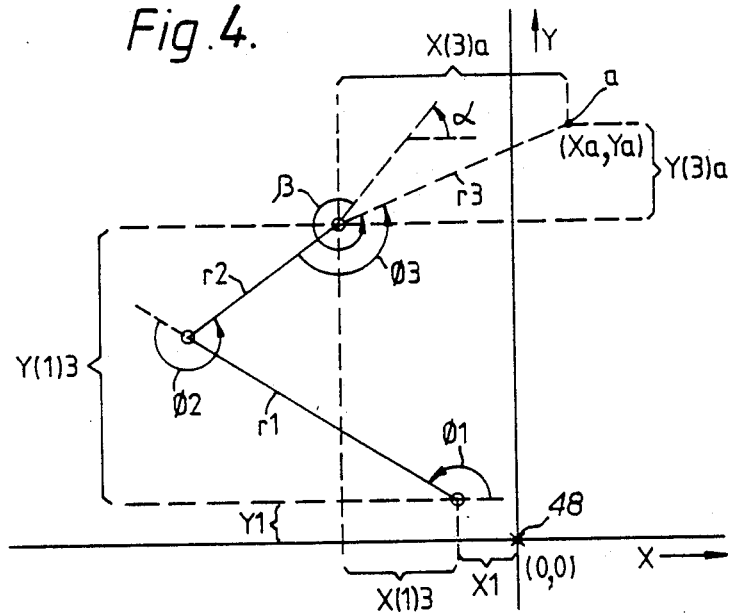
FIG. 4 is a diagram illustrating a forward transform factor field.

A main computing process in this conversion is the reverse transformation calculation represented by the block 143. The actual values phi1(act) and phi2(act) are sampled from the position sensors 116A and 104A and are applied to 143 where these values are used as indicated by equations (6) and (7) to generate actual values X(1)3(act) and Y(1)3(act). The constant values X1, Y1 relating to the origin offset (if any), and the quasi constant offset X(3)a, Y(3)a of the point a from the third axis X3, Y3 which will have been determined optically at the start and will be modified whenever the demand value of alpha (block 139) is changed, are supplied from corresponding memory locations 144 and 145, respectively. These offsets are added to the generated values X(1)3(act), Y(1)3(act) in accordance with equations (8) and (9) to provide actual coordinate values Xa(act) and Ya(act), relating to the patient reference point a. These operations are illustrated by FIG. 4.

The respective actual values Xa(act), Ya(act) are subtracted from the corresponding set-point demand values Xa(setp) and Ya(setp) provided by the control system 140, by a differencing process indicated by 146 and 147, respectively, to provide error quantities EX, EY representing the magnitude and sign of the cartesian error components. Before such error values can be applied to form a drive signal to the angular drive servos 131 and 132 the signs (polarities) of EX and EY must be related to the corresponding error (drive) signals Ephi1 and Ephi2 which would be required in each case to drive the corresponding servo 131, 132 in a direction which would tend to reduce the given error EX or EY. When the errors are not too large the appropriate polarity will be provided in each case by multiplying the cartesian error component EX, EY by the corresponding partial differential coefficient with respect to the relevant angle phi1 or phi2. These differential coefficients are given by equations (10), (11), (13) and (14) and are derived computationally as indicated by blocks 148, 149, 150 and 151. The respective subsequent multiplication steps are indicated by blocks 152, 153, 154 and 155 after which the modified error values relating to the same angle are added at 156 and 157 to provide angular error signals Ephi1 and Ephi2 as indicated by equations (15) and (16).

The differential coefficients ought strictly to relate to the coordinates and related angles represented by the set-point demand values Xa(setp), Ya(setp), however, when the servo errors are small and the system is following a series of closely adjacent values, it is sufficient to use differential coefficients calculated from the actual values of phi1 and phi2 since the relevant coefficients will tend towards the correct values as the null balance point is approached.

Calculation of the differential coefficients does not add significantly to the data processing time since the values of the sine and cosine terms will already have been derived for the basic transformation equations (8) and (9) and can be stored for subsequent use in equations (10), (11), (13) and (14). The additions required by equations (10) and (11) must be carried out to the full digital accuracy because for some combinations of angles the result will give small near-zero values from the difference of two relatively large values, and it is important for the value of the coefficient to pass through zero and to reverse in sign at the correct angular values to avoid an unnecessary amount of drive being applied to a rotation servo by a significant cartesian error signal relating to a coordinate which happens at that moment to be directed at right angles to, i.e. in quadrature with, that rotation. It is not however important that the absolute value of the resultant differential coefficient be followed exactly above about ten percent of the maximum amplitude, consequently a process of amplitude limitation can be applied enabling multiplication to take place using a smaller number of digits hence saving computing time.

Although the nulling servo arrangement described so far can function correctly when the set-point demand values applied are relatively close to the actual position values, difficulties arise when a large difference in position values is presented, for example as the result of a manual input command or an initial step or a large change in a treatment pattern. Thus it will be apparent from equations (15) and (16) that situations could occur where the EX and EY terms may be equal but opposite in sign giving rise to a zero angular drive in one of the servos while the errors are still large. In most cases this will only occur in one of the servo channels, and continued operation of the other servo would soon remove the balancing equality. There may also be instances when the resultant drive will tend to cause an angular displacement servo to start to move in the wrong direction as a result of calculating the differential coefficient from the actual angles and may even cause the drive to lock-up against an end stop in the case of phi1. Thus, because of the non-linear relationship between the cartesian coordinate values and the angles phi1 and phi2 it is desirable to provide a coarse angle control arrangement indicated by the dashed outline 160 which includes a coarse look-up table represented by the block 161, and which provides substitute drive signals to the servos 131 and 132 whenever either or both actual cartesian coordinate value, e.g. Xa(act), Ya(act), departs by more than a predetermined amount from the set-point demand values.

The look-up table 161 comprises a two-dimensionally organised storage facility, suitably implemented by a ROM or an EPROM matrix store, and can be addressed in accordance with the more significant digits representing the quantities X(1)3(setp) and Y(1)3(setp) derived from the values Xa(setp), Ya(setp) by subtracting the origin offset X1, Y1 and the patient reference point offset X(3)a, Y(3)a as indicated by blocks 162, 163. The addressed store 161 then outputs respective coarse values phi1c and phi2c which have been computed and adjusted on manufacture to provide initial demand angle settings for the servos 131 and 132 to aim for. The coarse values phi1C and phi2C are applied to respective differencing processes 164, 165 together with the actual values phi1(act), phi2(act) from the position sensors 116A, 104A so as to provide initial angular error (drive) signals Ephi1c, Ephi2c. The cartesian error signals EX, EY are applied to a comparison process 166 in which the absolute values of EX and EY are compared with a predetermined value k and when either or both exceed that value both switch processes 167 and 168 are changed over so that the error drive signals input to the servos 131 and 132 via the D/A converters 134, 135, are provided by the signals Ephi1c and Ephi2c formed from the coarse values generated by the look-up table 161. Once the servos 131, 132 have in this way been driven to the point at which EX, EY are both less than k, both the switches 167 and 168 revert to the original state and the nulling servo 142 operates as hereinbefore described.

The field of X(1)3, Y(1)3 values represented by the table 161 must, of course be more extensive than the required displacement field for the patient reference point a about the isocentre, and which could for example be about 1 m square, because allowance must be made for the range of variation to be expected in the patient reference point offset X(3)a, Y(3)a, and this might further amount to about 1 m square. Thus the maximum field required for the distances X(1)3, Y(1)3 represented in the look-up table 161 would be about 2 m square and both dimensions can each be satisfactorily divided into fifteen equal intervals giving a grid of 256 spot values. If the corresponding angles phi1 and phi2 are each coarsly represented by one byte (eight bits) at the related addresses, only about 1K of storage will be required, and the angles can be represented to within about 1.5 degrees.

The value of k employed in the comparison process 166 must be selected so as to ensure that for all the stored pairs of spot values of phi1 and phi2 in the look-up table, both EX and EY will fall below the value k well before both the servos 131 and 132 reach the stored demand values of phi1 and phi2 from any direction in the X(1)3, Y(1)3 field. Thus the value of k could be set at about ten percent of the maximum possible value representing X(1)3 or Y(1)3, and such a value should enable the nulling servo arrangement 142 to complete the positioning process without difficulty.

Modifications and alternatives to the control arrangement illustrated and described with reference to FIG. 5, can be employed. Thus, in determining the appropriate polarities for the cartesian error components EX and EY which are to be combined to form the angular error (drive) signals Ephi1 and Ephi2, the partial differential coefficients generated from the actual values of the angular positions phi1 and phi2, can be replaced by data relating to the appropriate polarities which is stored in a look-up table organised in a similar manner to the table 161. For example, the quantities X(1)3(setp) and Y(1)3(setp) can be employed to address a stored set of polarity coefficients, e.g. $-1, 0, +1$, relating to EX and EY, and to Ephi1 and Ephi2 near the corresponding null point of balance at the demand values X(1)3(setp) and Y(1)3(setp). The coefficient zero may be required when a respective quadrature control condition for either EX or EY lies within the expected balancing range. Preferably such a look-up table would also store coarse demand values for phi1 and phi2 as in the case of table 161, for use in a similar manner when either or both cartesian error values are large.

What is claimed is:

1. A patient support system for positioning a patient relative to an irradiation therapy or treatment simulation isocentre, comprising a main supporting arm rotationally attached at one end to a structural support by a first support bearing so as to be rotatable about a first first vertical axis, a further supporting arm rotationally attached at one end to the other end of the main supporting arm by a second support bearing so as to be rotatable about a second vertical axis, vertical support means rotationally attached to the other end of the further supporting arm by a third support bearing so as to be rotatable about a third vertical axis, the first, second and third axes each being provided with corresponding motor drives and associated angular position and angular velocity sensing means, a patient support table top attached to supporting carrier means, the vertical support means including means for locating and vertically displacing the supporting carrier means, and control means including computing means arranged to control the respective motor drives in response to the associated angular position and velocity sensing means and to corresponding position demand values, characterised in that the position demand values include horizontal x- and y-cartesian coordinate set-point demand values for a predetermined reference point associated with a patient on the patient support table top, relative to the isocentre, said computing means being arranged to calculate actual x- and y-coordinate values relating to said reference point from angular positions measured by the sensing means respectively associated with angular positions about at least two of said vertical axes, to compare these actual coordinate values using a differencing process, with the corresponding set-point cartesian coordinate demand values to form corresponding cartesian error values and to combine the corresponding cartesian error values so as to provide corresponding drive signals for the motor drives associated with rotation about said at least two vertical axes for reducing or nullifying said cartesian error values.

2. A patient support system as claimed in claim 1, characterised in that the motor drives are provided with electric drive motors.

3. A patient support system as claimed in claim 1, characterised in that the computing means comprises at least one microprocessor.

4. A patient support system as claimed in claim 1, characterised in that a look-up table is provided in a matrix organised memory which is addressed in accordance with cartesian coordinate demand values and which stores coarse set-point values for the angular positions about said at least two of said vertical axes for spaced spot values of pairs of X- and Y-coordinates over an operational field of values, and when either of the cartesian error values exceeds a predetermined threshold the respective coarse set-point angular position values recalled from memory are employed as demand values for the motor drives arranged as corresponding angular position set-point servos.

5. A patient support system as claimed in claim 4 wherein said computing means is arranged to combine the corresponding cartesian error values so as to provide corresponding drive signals for said motor drives for said at least two of said vertical axes, by for each vertical axis, adding products formed by multiplying each cartesian error value by a partial differential coefficient relating change of angular position about said each vertical axis to change of said each cartesian error value.

6. A patient support system as claimed in claim 5 wherein said at least two of said vertical axes are the first and second vertical axes.

7. A patient support system as claimed in claim 6, wherein said patient support table top has a horizontal longitudinal axis, and wherein said control means further comprising angular set-point servo means, responsive to a demand angular position of said longitudinal axis and to the sensing means, for controlling the angular orientation of said longitudinal axis by providing a drive signal to only the motor drive for the third axis.

8. A patient support system as claimed in claim 4 wherein said at least two of said vertical axes are the first and second vertical axes.

9. A patient support system as claimed in claim 8, wherein said patient support table top has a horizontal longitudinal axis, and wherein said control means further comprising angular set-point servo means, responsive to a demand angular position of said longitudinal axis and to the sensing means, for controlling the angular orientation of said longitudinal axis by providing a drive signal to only the motor drive for the third axis.

10. A patient support system as claimed in claim 1, characterised in that a look-up table is provided in a matrix organised memory which is addressed in accordance with cartesian coordinate demand values and which stores data representing a sign to be applied to each respective cartesian error value in providing the corresponding drive signals for the motor drives associated with rotation about said vertical axes, for spaced spot values of pairs of x- and y-coordinates over an operational field of values.

11. A patient support system as claimed in claim 1 wherein said computing means is arranged to combine the corresponding cartesian error values so as to provide corresponding drive signals for said motor drives for said at least two of said vertical axes, by for each vertical axis, adding products formed by multiplying each cartesian error value by a partial differential coefficient relating change of angular position about said each vertical axis to change of said each cartesian error value.

12. A patient support system as claimed in claim 11, characterised in that the differential coefficients are derived from the actual angular positions sensed by the sensing means.

13. A patient support system as claimed in claim 11 wherein said at least two of said vertical axes are the first and second vertical axes.

14. A patient support system as claimed in claim 13, wherein said patient support table top has a horizontal longitudinal axis, and wherein said control means further comprising angular set-point servo means, responsive to a demand angular position of said longitudinal axis and to the sensing means, for controlling the angular orientation of said longitudinal axis by providing a drive signal to only the motor drive for the third axis.

15. A patient support system as claimed in claim 1 wherein said at least two of said vertical axes are the first and second vertical axes.

16. A patient support system as claimed in claim 15, wherein said patient support table top has a horizontal longitudinal axis, and wherein said control means further comprising angular set-point servo means, responsive to a demand angular position of said longitudinal axis and to the sensing means, for controlling the angular orientation of said longitudinal axis by providing a drive signal to only the motor drive for the third axis.

* * * * *